US010471090B2

(12) United States Patent
Vogt et al.

(10) Patent No.: US 10,471,090 B2
(45) Date of Patent: Nov. 12, 2019

(54) POLYMER SOLUTION FOR VISCO-SUPPLEMENTATION

(71) Applicant: HERAEUS MEDICAL GMBH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

(*) Notice: Subject to any disclaimer, the term of this patent is extended or adjusted under 35 U.S.C. 154(b) by 0 days.

(21) Appl. No.: 15/599,523

(22) Filed: May 19, 2017

(65) Prior Publication Data
US 2017/0333469 A1 Nov. 23, 2017

(30) Foreign Application Priority Data

May 19, 2016 (DE) .......................... 10 2016 208 567

(51) Int. Cl.
A61K 31/715 (2006.01)
A61K 47/12 (2006.01)
A61K 9/00 (2006.01)
C08B 1/00 (2006.01)
A61K 45/06 (2006.01)
A61L 2/00 (2006.01)
A61K 31/65 (2006.01)
A61K 31/661 (2006.01)
A61K 31/7036 (2006.01)
A61K 31/717 (2006.01)
A61K 31/728 (2006.01)
A61K 31/795 (2006.01)
A61K 47/58 (2017.01)

(52) U.S. Cl.
CPC .......... A61K 31/715 (2013.01); A61K 9/0024 (2013.01); A61K 31/65 (2013.01); A61K 31/661 (2013.01); A61K 31/7036 (2013.01); A61K 31/717 (2013.01); A61K 31/728 (2013.01); A61K 31/795 (2013.01); A61K 45/06 (2013.01); A61K 47/12 (2013.01); A61K 47/585 (2017.08); A61L 2/0082 (2013.01); C08B 1/003 (2013.01)

(58) Field of Classification Search
CPC .... A61K 31/715; A61K 9/0024; A61K 47/12; A61K 31/795; A61K 31/728; A61K 45/06; C08B 1/003; A61L 2/0082
USPC .......................................................... 514/54
See application file for complete search history.

(56) References Cited

U.S. PATENT DOCUMENTS 4,588,583 A 5/1986 Pietsch et al.
4,782,046 A 11/1988 Brown et al.
8,563,243 B2 9/2013 Leonard et al.
8,829,073 B2 9/2014 Nies
9,387,275 B2 7/2016 Vogt et al.
9,457,110 B2 10/2016 Vogt
2009/0105144 A1 4/2009 Vogt et al.
2009/0105366 A1 4/2009 Vogt et al.
2011/0054392 A1 3/2011 Nies
2011/0237705 A1 9/2011 Leonard et al.
2011/0270259 A1 11/2011 Shim
2012/0289608 A1 11/2012 Sattig et al.
2013/0125786 A1 5/2013 Vogt
2013/0310466 A1 11/2013 Vogt
2014/0017223 A1 1/2014 Tijssen et al.
2015/0051305 A1 2/2015 Sattig et al.
2016/0346426 A1 12/2016 Vogt
2017/0173192 A1 6/2017 Vogt et al.

FOREIGN PATENT DOCUMENTS

| CA | 1 270 219 | 6/1990 |
| DE | 32 45 956 A1 | 6/1984 |
| DE | 100 32 118 A1 | 1/2002 |
| DE | 10 2007 015 698 A1 | 10/2008 |
| DE | 10 2007 052 116 A1 | 4/2009 |
| DE | 10 2007 050 762 B3 | 5/2009 |
| DE | 10 2008 030 312 A1 | 1/2010 |
| DE | 10 2009 043 550 A1 | 5/2011 |
| EP | 1 031 345 A1 | 3/2000 |
| EP | 2 664 349 A1 | 11/2013 |
| EP | 2 596 812 B1 | 6/2015 |
| EP | 3 184 550 A1 | 6/2017 |
| GB | 2 366 727 A | 3/2002 |
| JP | S 60 133894 A | 7/1985 |

(Continued)

OTHER PUBLICATIONS

Test material and applied methods Determination of the dough-forming time according to the ISO 5833 (1992) standard.
German Office Action issued in corresponding application dated Jan. 21, 2017.
Isoyama, et al.; "Differential Selectivity of Hyaluronidase Inhibitors Toward Acidic and Basic Hyaluronidases"; Glycobiology, vol. 16, No. 1, pp. 11-21, 2005.
European Search Report from corresponding EP application 17165209.2 dated Sep. 26, 2017.
Hoffman et. al., "Beta-Propiolactone Vapor as a Disinfectamt"; Appl. Microbiol. Sep. 1958; 6 (5), pp. 358-362.
Borick,"Chemical Sterilizers (Chemosterilizers)" Adv. Appl. Microbiol. 10 (1968), pp. 291-312.

(Continued)

Primary Examiner — Yih-Horng Shiao
(74) Attorney, Agent, or Firm — Norris McLaughlin, P.A.

(57) ABSTRACT

The invention proposes a polymer solution for visco-supplementation. The polymer solution contains at least one at least partially water-soluble polysaccharide or polysaccharide derivative, one water-soluble alkali salt or alkaline earth salt of polystyrene sulfonic acid, and water, whereby the polymer solution is clear to the eye. Moreover, the invention describes a method for sterilization of the polymer solution. This method is characterized in that a mixture of at least one at least partially water-soluble polysaccharide or polysaccharide derivative, one water-soluble alkali salt or alkaline earth salt of polystyrene sulfonic acid, and water is mixed with at least 0.5 wt. % ß-propiolactone, and in that the polymer solution is stored at room temperature for at least 24 hours.

14 Claims, No Drawings

(56) References Cited

FOREIGN PATENT DOCUMENTS

| JP | 2013 522285 A | 6/2013 |
| WO | 2009 103123 A1 | 8/2009 |
| WO | WO 2014/153238 A2 * | 9/2014 |

OTHER PUBLICATIONS

Gould, "Recent Advances in the Understanding of Resistance and Dormancy in Bacterial Spores", Journal of Applied Bacteriology 1977, 42, pp. 297-309.
Gould, "Mechanisms of Resistance and Dormancy"; The Bacterial Spor, vol. 2, Academic Press, 1983, pp. 173-209.

* cited by examiner

POLYMER SOLUTION FOR VISCO-SUPPLEMENTATION

This application claims priority of German patent application No. DE 102016208567.0, filed May 19, 2016, the entire contents of which are incorporated herein by reference.

The subject matter of the invention is a polymer solution for visco-supplementation, especially for the treatment of arthrosis.

Arthrosis (*Arthrosis deformans*) is a widespread degenerative disease of the joints. It is associated with damage (erosion) to the cartilage surfaces, detachment of cartilage particles, and inflammation of the synovial membrane caused by cartilage particles. In cases of mild and moderate arthrosis, attempts have been made for a number of years to use in intra-articular injection of hyaluronic acid (visco-supplementation) to improve the pain status of the patients and simultaneously to reduce the progression of the arthrosis.

Hyaluronic acid is a natural ingredient of the fluid in joints (synovial fluid). Hyaluronic acid acts as a lubricant in the synovial fluid. It is particularly advantageous that aqueous hyaluronic acid solutions are visco-elastic. This results in very good lubricating and gliding properties.

Based on the advantageous lubrication properties, aqueous hyaluronic acid solutions have been used for visco-supplementation for nearly two decades. According to the current prior art, hyaluronic acid produced by fermentation is used. Besides, the use of water-soluble cellulose derivatives, such as carboxymethylcellulose and methylcellulose, [and] of starch derivatives, such as hydroxyethyl starch, for visco-supplementation also appears feasible as a matter of principle.

It is customary to use a sterile aqueous hyaluronic acid solution for visco-supplementation. One problem associated with the use of aqueous solutions of hyaluronic acids is that these are enzymatically degraded by inherent hyaluronidases relatively shortly after injection into the articular space and that the desired lubricating effect decreases due to this process. Accordingly, aqueous polymer solutions that are more stable with respect to the inherent hyaluronidases are desired.

The object of the invention is the development of an aqueous polymer solution that contains at least partially water-soluble polymers that cannot be degraded by hyaluronidases. The polymer solution to be developed should be more stable with respect to hyaluronidase as compared to aqueous hyaluronic acid solutions.

It is another object of the invention to find combinations of at least partially water-soluble polymers that are compatible with each other in aqueous solution. This means that these polymer combinations must not lead to flocculation of one or both polymers in aqueous solution. The polymer combinations must form aqueous polymer solutions that are clear to the eye.

It is another object of the invention to develop a method for sterilisation of the polymer solution to be developed. Said method shall enable sterilisation without any discolouration of the polymer solutions. The sterilisation method must ensure that the two at least partially water-soluble polymers do not flocculate from the polymer solution due to the sterilisation process and that the polymers continue to stay in solution.

The object of the invention is met according to claim 1.

A polymer solution for visco-supplementation, especially for the treatment of arthrosis, is inventive. Said polymer solution contains a) at least one at least partially water-soluble polysaccharide or polysaccharide derivative or a mixture of at least one at least partially water-soluble polysaccharide and at least one at least partially water-soluble polysaccharide derivative;

b) at least one water-soluble alkali salt or alkaline earth salt of polystyrene sulfonic acid; and c) water.

It has been found, surprisingly, that aqueous polymer solutions containing water-soluble polysaccharides, such as hyaluronic acid, and water-soluble polysaccharide derivatives, such as carboxymethylcellulose, methylcellulose, and hydroxyethyl cellulose, and alkali salts and alkaline earth salts of polystyrene sulfonic acids form non-flocculating solutions that are clear to the eye. Moreover, it was found that aqueous solutions containing hyaluronic acid and alkali salts or alkaline earth salts of polystyrene sulfonic acid are stable with respect to degradation by hyaluronidases.

Likewise, a polymer solution consisting of a) at least one at least partially water-soluble polysaccharide or at least one at least partially water-soluble polysaccharide derivative or a mixture of at least one at least partially water-soluble polysaccharide and at least one at least partially water-soluble polysaccharide derivative;

b) at least one water-soluble alkali salt or alkaline earth salt of polystyrene sulfonic acid;

c) water;

d) optionally, 3-hydroxypropionic acid;

e) optionally, at least one antiphlogistic agent;

f) optionally, at least one antibiotic;

g) optionally, at least one immunosuppressant;

h) optionally, at least one cytostatic agent is also inventive.

A polymer solution containing a) at least one at least partially water-soluble polysaccharide or polysaccharide derivative;

b) at least one water-soluble alkali salt or alkaline earth salt of polystyrene sulfonic acid;

c) water; and d) 3-Hydroxypropionic acid is also inventive.

According to the invention, the polysaccharides are natural polysaccharides and polysaccharide derivatives. According to the invention, polysaccharide derivatives shall be understood to be salts, ethers, esters of the acids or esters, in particular alkali metal salts, in particular sodium and potassium salts, of polysaccharides. Examples include alginic acid, sodium alginate, hyaluronic acid, the sodium salt of hyaluronic acid, carboxymethylcellulose, the sodium salt of carboxymethylcellulose, hydroxyethyl cellulose, cellulose ether, starch, starch ether, guar, chitin, chitosan.

Preferably, the polysaccharide or polysaccharide derivative is selected from the group consisting of the sodium salt of hyaluronic acid, the sodium salt of carboxymethylcellulose, hydroxyethyl cellulose, hydroxyethyl starch, and methylcellulose.

According to the invention, the polysaccharides and polysaccharide derivatives can just as well be mixtures of said polysaccharides or mixtures of said polysaccharide derivatives or mixtures of at least one of said polysaccharides and at least one of said polysaccharide derivatives.

The molar mass $M_n$ of the polysaccharide and polysaccharide salts preferably ranges from 20,000 to 3,000,000 Dalton. Particularly preferably, it ranges from 50,000 to 2,000,000 Dalton.

The molar mass $M_n$ of the hyaluronic acid salt preferably ranges from 100,000 to 2,000,000 Dalton. Particularly preferably, it ranges from 500,000 to 1,500,000 Dalton.

According to the invention, the polystyrene sulfonic acid salt is the salt of a polymer with the following structural units:

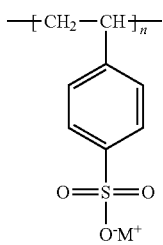

In this context, n represents the number of repeating structural units and $M^+$ stands for alkali and alkaline earth ions. Polystyrene sulfonic acid salts preferably have a molar mass $M_n$ ranging from 20,000 to 3,000,000 Dalton. Preferably, the polystyrene sulfonic acid salt has a mean molar mass $M_n$ ranging from 50,000 to 2,000,000 Dalton.

Sodium, potassium, and magnesium salts are preferred as alkali and alkaline earth salts of the polystyrene acid. Sodium and potassium salts are particularly preferred.

The polymer solution is characterised in that the mass ratio of polysaccharide or of polysaccharide derivative or of said mixtures and alkali salt or alkaline earth salt of polystyrene sulfonic acid is 1.0 to 1.0 to 1 to 0.0001.

Preferably, the total polymer content of the polymer solution ranges from 0.1 to 10 wt. %, particularly preferably ranges from 0.25 to 5 wt. %.

It is advantageous for the polymer solution to contain at least one antiphlogistic agent, at least one antibiotic, at least one antisuppressant, at least one cytostatic agent or a mixture of said agents.

The at least one antiphlogistic agent is preferably selected from the group consisting of non-steroidal antiphlogistic agents and glucocorticoids. Pertinent examples include acetylsalicylic acid, ibuprofen, diclofenac, ketoprofen, dexamethasone phosphate, triamcinolone, prednisone, hydrocortisone, hydrocortisone acetate, and fluticason. Particularly preferably, the at least one antiphlogistic agent selected from the group consisting of dexamethasone phosphate and triamcinolone.

The polymer solution can contain common antibiotics, such as gentamicin sulfate. Other examples include aminoglycoside antibiotics and lincosamide antibiotics. However, the at least one antibiotic preferably is selected from the group consisting of tetracycline antibiotics, particularly preferably it is selected from the group consisting of doxycycline, chlorotetracycline, and oxytetracycline.

Moreover, immunosuppressants and cytostatic agents can be contained therein. Particularly preferred examples include doxorubicin, ciclosporin, methotrexate, leflunomide, azathioprin, mitomycin C, tacrolimus, sirolimus, and everolimus.

It is particularly preferred for the polymer solution to contain at least one agent selected from the group consisting of dexamethasone phosphate, triamcinolone, doxycyclin, chlorotetracyclin, oxytetracyclin, doxorubicin, ciclosporin, methotrexate, leflunomide, azathioprin, mitomycin C, tacrolimus, sirolimus, and everolimus.

The antiphlogistic agents, in particular dexamethasone phosphate and triamcinolone, can have a beneficial effect on the inflammation processes in the damaged cartilage tissue during the use of the polymer solution for visco-supplementation. Moreover, immunosuppressants, such as mitomycin C, tacrolimus, sirolimus, and everolimus, can be added to the polymer solution to advantage. According to the invention, antibiotics, such as doxycycline, chlorotetracycline, oxytetracycline, can be added to the polymer solution just as well.

The hyaluronic acid solutions used for visco-supplementation thus far were predominantly sterilised by means of gamma irradiation. Dosages equal to/more than 25 kGy are customary in this context. The sterilisation is done on finally packaged hyaluronic acid solution. However, the exposure to gamma radiation is associated with grave disadvantages. Exposure to gamma radiation degrades the polymer chains, which reduces the molar mass clearly and generates low molecular weight degradation products. Moreover, the packaging means, usually disposable syringes made of plastic, may become brittle because of the gamma radiation. Moreover, discolourations of the hyaluronic acid solutions may occur due to side reactions. Especially the polymer degradation depends largely on the dosage of the gamma radiation. Common gamma sources have a spherical radiation field. This means that the incident doss can vary as a function of the position of the object to be sterilised. By this means, the polymer degradation never proceeds uniformly and inhomogeneities in the final viscosity are possible. It is difficult to attain a reproducible final viscosity of the sterilised hyaluronic acid solutions.

An alternative sterilisation method is the steam sterilisation of aqueous hyaluronic acid solutions, which can lead to damage to the hyaluronic acid and the plastic packaging means though. Due to the relatively high viscosity of the solutions, sterile filtration of aqueous hyaluronic acid solutions is basically not feasible or only with an inordinate effort. Sterile filtration removes microbial life forms only from a certain size. Viruses cannot be removed or inactivated by sterile filtration.

Aside from said physical sterilisation methods, it is also customary to use chemical compounds for sterilisation of medical products. These include formaldehyde, glutardialdehyde, o-phthaldialdehyde. Sterilisation by means of aldehydes is disadvantageous in that these need to be removed again after the sterilisation in order to prevent harmful effects during the use in humans. This precludes the sterilisation of final packaged aqueous hyaluronic acid solutions with aldehydes, since these cannot be removed again from the final packaged hyaluronic acid solutions.

Oxidising agents, such as hydrogen peroxide, performic acid, peracetic acid, hypochloride, and hypochloride-releasing substances, such as chloramine T 2 or trichloroisocyanuric acid, are very effective sterilisation means. These agents are disadvantageous in that they cause significant oxidative degradation of the dissolved hyaluronic acid. Moreover, non-reacted residues of the oxidising agents may remain in the hyaluronic acid solution in its final packaging and may possibly have a local toxic effect.

It is known from pharmaceutical industry that aqueous protein solutions, such as, e.g., vaccines, are very sensitive to the effects of oxidising sterilisation agents and various physical sterilisation methods, for example sterilisation with gamma radiation. For this reason, these aqueous protein solutions are subjected to sterile filtration first and then have small amounts of ß-propiolactone added to inactivate viruses. ß-propiolactone acylates the amino groups of the DNA/RNA or proteins of the viruses. The water that is present as solvent is capable of slowly decomposing ß-propiolactone such that no active ß-propiolactone is present any longer in aqueous protein solutions after just a short period of time. It is known thus far that gaseous ß-propiolactone can irreversibly inactivate endospores (R. K. Hoffmann, B. Warshowsky: Beta-Propiolactone Vapor as a Disinfectant. Appl. Microbiol. 1958 September; 6 (5): 358-362). Moreover, ß-propiolactone is known to inactivate endospores in non-aqueous organic monomers/monomer mixtures and pasty cements containing organic monomers (EP 2 596 812 B1).

However, aside from the vegetative forms, micro-organisms also have generative forms, such as endospores. These generative survival forms of micro-organisms are formed by gram-positive bacteria, in particular of the Bacillus and Clostridium genera, as a means of persisting during unfavourable living conditions. In their resting state, endospores have no active metabolism and possess a multi-layered spore capsule that largely protects the core of the spore from the action of chemicals and other environmental effects. This renders spores extremely resistant to the action of heat and chemicals (Borick, P. M.: Chemical sterilizers. Adv. Appl. Microbiol. 10 (1968) 291-312; Gould, G. W.: Recent advances in the understanding of resistance and dormancy in bacterial spores. J. Appl. Bacteriol. 42 (1977) 297-309; Gould, G. W.: Mechanisms of resistance and dormancy. p. 173-209. In Hurst, A. and Gould, G. W. (ed.), The bacterial spore. vol. 2 Academic Press, Inc. New York, 1983). Due to their high resistance, endospores are used as bio-indicators for validation and control of the efficacy of sterilisation processes. This is based on the assumption that the inactivation of endospores is indicative of all vegetative microbial forms of life being killed. Endospores of gram-positive bacteria are classified in international resistance class III. Resistance classes I include non-spore-forming bacteria and vegetative forms of spore-forming bacteria and resistance class II includes spores that are killed within a few minutes in a flow of steam at 105° C. In accordance with DAB 2008 (Deutsches Arzneimittelbuch), all micro-organisms of resistance classes I-Ill must be killed or inactivated irreversibly in the course of a sterilisation.

Moreover, the method for sterilisation of the polymer solution according to the invention is also inventive. This method is characterised in that a mixture is prepared that contains at least one at least partially water-soluble polysaccharide or polysaccharide derivative, one water-soluble alkali salt or alkaline earth salt of polystyrene sulfonic acid, and water and at least 0.5 wt. % ß-propiolactone, and in that the polymer solution is stored at 4-40° C. for at least 24 hours. It has been evident, surprisingly, that the sterilisation of the polymer solution according to the invention with ß-propiolactone is successful without attendant undesired discolouration. Moreover, it has been evident, surprisingly, that the sterilisation with ß-propiolactone is not associated with precipitation in polymer solutions that contain hyaluronic acid, carboxymethylcellulose, methylcellulose, hydroxyethyl cellulose in combination with polystyrene sulfonic acid, but that these stay dissolved and clear to the eye.

It is preferred to use 0.5-2.0 wt. % ß-propiolactone for sterilisation of the aqueous polymer solution. Safe inactivation of endospores is assured in this concentration range.

The polymer solution according to the invention is being provided as a means for visco-supplementation and as a support for pharmaceutical agents.

The invention is illustrated through the examples presented in the following, though without limiting the scope of the invention.

The following polysaccharides and/or polysaccharide derivatives were used in the experiments described hereinafter:

NaHya: Sodium salt of hyaluronic acid ($M_n$~0.9 million Dalton),

CMC: Sodium salt of carboxymethylcellulose ($M_n$~90,000 Dalton),

MC: Methylcellulose (SM-4000),

HEC: Hydroxyethylcellulose (60SH-4000)

PSS1: Sodium salt of polystyrene sulfonic acid ($M_n$~70,000 Dalton)

PSS2: Sodium salt of polystyrene sulfonic acid ($M_n$~1,300,000 Dalton)

A phosphate buffer with a pH value of 7.4 was prepared. For this purpose, 1.65 g potassium hydrogenphosphate and 9.71 g disodium hydrogenphosphate dihydrate were dissolved in 1 liter of distilled water.

EXAMPLE 1

A total of 5.0 ml of the phosphate buffer at a pH of 7.4 were placed in beaded rim vials. A total of 0.25 wt. %, 0.5 wt. %, 1.0 wt. %, and 2.0 wt. % polysaccharide/polysaccharide derivative and the sodium salt of polystyrene sulfonic acid (PSS1 and PSS2) were dissolved in these buffer solutions at room temperature. The polymer solutions were inspected visually after 24 hours.

| Polymer solution | Composition of the polymer solution | | Appearance |
|---|---|---|---|
| 1 | 0.25 wt. % NaHya | 0.25 wt. % PSS1 | clear to the eye |
| 2 | 0.25 wt. % CMC | 0.25 wt. % PSS1 | clear to the eye |
| 3 | 0.25 wt. % MC | 0.25 wt. % PSS1 | clear to the eye |
| 4 | 0.25 wt. % HEC | 0.25 wt. % PSS1 | clear to the eye |
| 5 | 0.25 wt. % NaHya | 0.25 wt. % PSS2 | clear to the eye |
| 6 | 0.25 wt. % CMC | 0.25 wt. % PSS2 | clear to the eye |
| 7 | 0.25 wt. % MC | 0.25 wt. % PSS2 | clear to the eye |
| 8 | 0.25 wt. % HEC | 0.25 wt. % PSS2 | clear to the eye |
| 9 | 0.5 wt. % NaHya | 0.5 wt. % PSS1 | clear to the eye |
| 10 | 0.5 wt. % CMC | 0.5 wt. % PSS1 | clear to the eye |
| 11 | 0.5 wt. % MC | 0.5 wt. % PSS1 | clear to the eye |
| 12 | 0.5 wt. % HEC | 0.5 wt. % PSS1 | clear to the eye |
| 13 | 0.5 wt. % NaHya | 0.5 wt. % PSS2 | clear to the eye |
| 14 | 0.5 wt. % CMC | 0.5 wt. % PSS2 | clear to the eye |
| 15 | 0.5 wt. % MC | 0.5 wt. % PSS2 | clear to the eye |
| 16 | 0.5 wt. % HEC | 0.5 wt. % PSS2 | clear to the eye |
| 17 | 1.0 wt. % NaHya | 1.0 wt. % PSS1 | clear to the eye |
| 18 | 1.0 wt. % CMC | 1.0 wt. % PSS1 | clear to the eye |
| 19 | 1.0 wt. % MC | 1.0 wt. % PSS1 | clear to the eye |
| 20 | 1.0 wt. % HEC | 1.0 wt. % PSS1 | clear to the eye |
| 21 | 1.0 wt. % NaHya | 1.0 wt. % PSS2 | clear to the eye |
| 22 | 1.0 wt. % CMC | 1.0 wt. % PSS2 | clear to the eye |
| 23 | 1.0 wt. % MC | 1.0 wt. % PSS2 | clear to the eye |
| 24 | 1.0 wt. % HEC | 1.0 wt. % PSS2 | clear to the eye |

EXAMPLE 2

Polymer solutions were prepared analogous to example 1, but also contained, in addition, the antibiotic doxycycline. Doxycycline-hyalate (doxycycline hydrochloride-hemiethanolate-hemihydrate) was used for this purpose. The polymer solutions were checked visually after 24 hours of storage at room temperature.

| Polymer solution | Composition of the polymer solution | | | Appearance |
|---|---|---|---|---|
| 25 | 0.5 wt. % NaHya | 0.5 wt. % PSS1 | 0.01 wt. % Doxycycline-hyalate | clear to the eye |
| 26 | 0.5 wt. % CMC | 0.5 wt. % PSS1 | 0.01 wt. % Doxycycline-hyalate | clear to the eye |
| 27 | 0.5 wt. % MC | 0.5 wt. % PSS1 | 0.01 wt. % Doxycycline-hyalate | clear to the eye |
| 28 | 0.5 wt. % HEC | 0.5 wt. % PSS1 | 0.01 wt. % Doxycycline-hyalate | clear to the eye |

EXAMPLE 3

Polymer solutions were prepared analogous to example 1, but also contained, in addition, the antibiotic gentamicin sulfate. Gentamicin sulfate (with an activity coefficient of 580) was used for this purpose. The polymer solutions were checked visually after 24 hours of storage at room temperature.

| Polymer solution | Composition of the polymer solution | | | Appearance |
|---|---|---|---|---|
| 25 | 0.5 wt. % NaHya | 0.5 wt. % PSS1 | 0.01 wt. % gentamicin sulfate- | clear to the eye |
| 26 | 0.5 wt. % CMC | 0.5 wt. % PSS1 | 0.01 wt. % gentamicin sulfate- | clear to the eye |
| 27 | 0.5 wt. % MC | 0.5 wt. % PSS1 | 0.01 wt. % gentamicin sulfate- | clear to the eye |
| 28 | 0.5 wt. % HEC | 0.5 wt. % PSS1 | 0.01 wt. % gentamicin sulfate- | clear to the eye |

EXAMPLE 4

Polymer solutions were prepared analogous to example 1, but also contained, in addition, the antiphlogistic agent dexamethasone phosphate. The sodium salt of dexamethasone phosphate (NaDexP) was used for this purpose. The polymer solutions were checked visually after 24 hours of storage at room temperature.

| Polymer solution | Composition of the polymer solution | | | Appearance |
|---|---|---|---|---|
| 25 | 0.5 wt. % NaHya | 0.5 wt. % PSS1 | 0.01 wt. % NaDexP | clear to the eye |
| 26 | 0.5 wt. % CMC | 0.5 wt. % PSS1 | 0.01 wt. % NaDexP | clear to the eye |
| 27 | 0.5 wt. % MC | 0.5 wt. % PSS1 | 0.01 wt. % NaDexP | clear to the eye |
| 28 | 0.5 wt. % HEC | 0.5 wt. % PSS1 | 0.01 wt. % NaDexP | clear to the eye |

EXAMPLE 5

A 0.25 wt. % solution of NaHya was prepared using phosphate buffer pH 7.4. Then 10 mg, 1.0 mg, 0.1 mg, and 0.01 mg PSS1 were added to 40.0 g of the solution each. For the addition of 0.1 mg and 0.01 mg PSS1, a solution of 10 mg PSS1 in phosphate buffer was prepared and corresponding aliquots of this solution were added to the NaHya solution. A solution containing 26.7 IU/μl of a bovine hyaluronidase (Kraeber, 329 IU/mg) in phosphate buffer pH 7.4 was prepared. Then, 150 μl aliquots of this hyaluronidase solution were added to 40 g of the NaHya-PSS1 solutions. The solutions were then maintained at 37° C. for 15 minutes in an Ubbelohde viscometer (capillary I). Then the passage time of the polymer solution was determined. The polymer solutions were then kept at 37° C. in the Ubbelohde viscometer. The passage time of the polymer solution was measured again in successive one-hour intervals. In addition, the passage time of a 0.25 wt. % NaHya solution with added hyaluronidase was measured as a reference.

| Composition of the 0.25 wt. % NaHY polymer solutions | | | | | | |
|---|---|---|---|---|---|---|
| NaHya | 0.25 wt. % | 0.25 wt. % | 0.25 wt. % | 0.25 wt. % | 0.25 wt. % | 0.25 wt. % |
| Hyaluronidase | − | + | + | + | + | + |
| PSS1 | — | — | 0.025 wt. % | 0.0025 wt. % | 0.00025 wt. % | 0.000025 wt. % |

| Time [h] | Passage time [min] | | | | | |
|---|---|---|---|---|---|---|
| 0.25 | 19 min 12 s | 12 min 28 s | 22 min 5 s | 22 min 20 s | 18 min 56 s | 9 min 14 s |
| 1.0 | 19 min 26 s | 7 min 16 s | 22 min 0 s | 22 min 5 s | 19 min 1 s | 6 min 15 s |
| 2.0 | 19 min 17 s | 5 min 26 s | 21 min 50 s | 21 min 58 s | 19 min 12 s | 4 min 52 s |
| 3.0 | 19 min 19 s | 4 min 31 s | 21 min 42 s | 22 min 3 s | 19 min 13 s | 3 min 56 s |
| 4.0 | 19 min 11 s | 3 min 55 s | 21 min 40 s | 22 min 6 s | 19 min 13 s | 3 min 31 s |
| 5.0 | 19 min 10 s | 3 min 31 s | 21 min 44 s | 22 min 11 s | 19 min 22 s | 3 min 10 s |

The passage times of the polymer solutions are proportional to the molar mass of the dissolved polymers. A reduction of the passage time is related to a decrease of the molar masses. The results show that polymer solutions containing hyaluronic acid and polystyrene sulfonic acid basically show no reduction of the passage times in the Ubbelohde viscometer within the test period of 5 hours. The hyaluronic acid contained in the polymer solution is obviously not being degraded by the hyaluronidase.

For a control, the influence of the hyaluronidase on the polystyrene sulfonic acid was investigated in another experiment. The experimental set-up was the same as in the preceding experiment.

| Composition of the polymer solutions | | |
|---|---|---|
| PSS1 | 0.25 wt. % | — |
| PSS2 | — | 0.25 wt. % |
| Time [h] | Passage time [min] | |
| 0.25 | 1 min 36 s | 4 min 28 s |
| 1 | 1 min 37 s | 4 min 27 s |
| 2 | 1 min 37 s | 4 min 29 s |
| 3 | 1 min 36 s | 4 min 26 s |
| 4 | 1 min 37 s | 4 min 28 s |
| 5 | 1 min 37 s | 4 min 26 s |

The results showed that aqueous polystyrene sulfonic acid solution cannot be degraded by hyaluronidase at 37° C.

EXAMPLE 6

A 0.25 wt. % solution of NaHya was prepared using phosphate buffer pH 7.4. Then 10 mg, 1.0 mg, 0.1 mg, and 0.01 mg PSS2 were added to 40.0 g of the solution each. For the addition of 0.1 mg and 0.01 mg PSS2, a solution of 10 mg PSS2 in phosphate buffer was prepared and corresponding aliquots of this solution were added to the NaHya solution. A solution containing 26.7 IU/µl of a bovine hyaluronidase (Kraeber, 329 IU/mg) in phosphate buffer pH 7.4 was prepared. Then, 150 µl aliquots of this hyaluronidase solution were added to 40 g of the NaHya-PSS2 solutions. The solutions were then maintained at 37° C. for 15 minutes in an Ubbelohde viscometer (capillary I). Then the passage time of the polymer solution was determined. The polymer solutions were kept at 37° C. in the Ubbelohde viscometer for this purpose. The passage time of the polymer solution was measured again in successive one-hour intervals. In addition, the passage time of a 0.25 wt. % NaHya solution with added hyaluronidase was measured as a reference.

| Composition of the 0.25 wt. % NaHY polymer solutions | | | | | | |
|---|---|---|---|---|---|---|
| NaHya | 0.25 wt. % | 0.25 wt. % | 0.25 wt. % | 0.25 wt. % | 0.25 wt. % | 0.25 wt. % |
| Hyaluronidase | − | + | + | + | + | + |
| PSS2 | — | — | 0.025 wt. % | 0.0025 wt. % | 0.00025 wt. % | 0.000025 wt. % |
| Time [h] | Passage time [min] | | | | | |
| 0.25 | 19 min 12 s | 12 min 28 s | 19 min 52 s | 22 min 26 s | 22 min 12 s | 18 min 17 s |
| 1.0 | 19 min 26 s | 7 min 16 s | 20 min 2 s | 22 min 16 s | 22 min 5 s | 18 min 05 s |
| 2.0 | 19 min 17 s | 5 min 26 s | 19 min 50 s | 22 min 24 s | 22 min 3 s | 18 min 10 s |
| 3.0 | 19 min 19 s | 4 min 31 s | 19 min 57 s | 22 min 24 s | 22 min 5 s | 17 min 58 s |
| 4.0 | 19 min 11 s | 3 min 55 s | 19 min 53 s | 22 min 22 s | 22 min 3 s | 18 min 5 s |
| 5.0 | 19 min 10 s | 3 min 31 s | 20 min 1 s | 22 min 23 s | 22 min 4 s | 18 min 7 s |

The passage times of the polymer solutions are proportional to the molar mass of the dissolved polymers. A reduction of the passage time is related to a decrease of the molar masses. The results show that polymer solutions containing hyaluronic acid and polystyrene sulfonic acid basically show no reduction of the passage times in the Ubbelohde viscometer within the test period of 5 hours. Obviously, the hyaluronic acid in the hyaluronic acid/polystyrene sulfonic acid solutions is not being degraded by the hyaluronidase.

EXAMPLE 7

Firstly, solutions of the polysaccharides containing polystyrene sulfonic acid were prepared using 30.0 mL phosphate buffer (pH value 7.4) each. A total of $10^6$ cfu of a spore suspension of *Bacillus atropheus* were added to 5.0 mL each of the polysaccharide solutions in a sterile 25 mL plastic tube. Then the spores were suspended homogeneously using a vortex mixer. Subsequently, 0.5 wt. %, 1.0 wt. %, and 2.0 wt. % ß-propiolactone were added to 5.0 mL each of the polysaccharide solution previously mixed with the spores. The sample was then homogenised again in a vortex mixer. Polysaccharide solutions not treated with ß-propiolactone were used as positive control. After 48 hours of storage at room temperature, the polysaccharide solutions were tested for sterility in accordance with DIN EN ISO 11737, part 2. The assays were done in duplicate.

| Composition of the polymer solution | | Result of the test of sterility Concentration of β-propiolactone [wt. %] | | | |
|---|---|---|---|---|---|
| | | 0.0 (positive control) | 0.5 | 1.0 | 2.0 |
| 0.5 wt. % NaHya | 0.5 wt. % PSS1 | +/+ | −/− | −/− | −/− |

-continued

| Composition of the polymer solution | | Result of the test of sterility Concentration of β-propiolactone [wt. %] | | | |
|---|---|---|---|---|---|
| | | 0.0 (positive control) | 0.5 | 1.0 | 2.0 |
| 0.5 wt. % CMC | 0.5 wt. % PSS1 | +/+ | −/− | −/− | −/− |
| 0.5 wt. % MC | 0.5 wt. % PSS1 | +/+ | −/− | −/− | −/− |
| 0.5 wt. % HEC | 0.5 wt. % PSS1 | +/+ | −/− | −/− | −/− |
| 0.5 wt. % NaHya | 0.5 wt. % PSS2 | +/+ | −/− | −/− | −/− |
| 0.5 wt. % CMC | 0.5 wt. % PSS2 | +/+ | −/− | −/− | −/− |
| 0.5 wt. % MC | 0.5 wt. % PSS2 | +/+ | −/− | −/− | −/− |
| 0.5 wt. % HEC | 0.5 wt. % PSS2 | +/+ | −/− | −/− | −/− |

(+) growth
(−) no growth

The polysaccharide solutions sterilised with ß-propiolactone showed no discolouration whatsoever as compared to the untreated polysaccharide solutions used as positive control.

The invention claimed is:

1. A polymer solution comprising:
   a) at least one hyaluronic acid or hyaluronic acid derivative having a molar mass $M_n$ ranging from 20,000 to 3,000,000 Dalton;
   b) at least one water-soluble alkali salt or alkaline earth salt of polystyrene sulfonic acid; and
   c) water;
   wherein the polymer solution comprises a) and b) in a mass ratio of a):b) of 1:1 to 1:0.001; and
   wherein the polymer solution is suitable for visco-supplementation.

2. The polymer solution according to claim 1, further comprising:
   d) 3-hydroxypropionic acid.

3. The polymer solution according to claim 1, wherein the solution is clear to the eye.

4. The polymer solution according to claim 1, wherein the mass ratio of a):b) is 1:1 to 1:0.01.

5. The polymer solution according to claim 1, wherein the total polymer content of the polymer solution is 0.1 to 10 wt. %.

6. The polymer solution according to claim 1, wherein the polymer solution further comprises at least one distinct agent selected from the group consisting of antiphlogistic agents, antibiotics, immunosuppressants, and cytostatic agents.

7. The polymer solution according to claim 6, wherein the polymer solution comprises at least one of dexamethasone phosphate, triamcinolone phosphate, doxycycline, chlorotetracycline, oxytetracycline, doxorubicine, cyclosporine, methotrexate, leflunomide, azathioprine, mitomycin C, tacrolimus, sirolimus, and everolimus.

8. The polymer solution according to claim 1, wherein the polymer solution consists of:
   a) at least one hyaluronic acid or hyaluronic acid derivative having a molar mass Mn ranging from 20,000 to 3,000,000 Dalton;
   b) at least one water-soluble alkali salt or alkaline earth salt of polystyrene sulfonic acid;
   c) water; and
   d) optionally, 3-hydroxypropionic acid; and
   e) optionally, at least one distinct agent selected from the group consisting of antiphlogistic agents, antibiotics, immunosuppressants, and cytostatic agents.

9. A method for producing a sterile aqueous polymer solution, comprising mixing the following ingredients:
   a) at least one hyaluronic acid or hyaluronic acid derivative having a molar mass Mn ranging from 20,000 to 3,000,000 Dalton;
   b) one water-soluble alkali salt or alkaline earth salt of polystyrene sulfonic acid;
   c) water; and
   d) at least 0.5 wt. % ß-propiolactone;
   wherein a) and b) are in a mass ratio of a):b) of 1:1 to 1:0.001;
   to form a polymer solution suitable for visco-supplementation; and
   storing the polymer solution thus prepared for at least 24 hours at 4-40° C.

10. The method according to claim 9, wherein 0.5-2.0 wt. % ß-propiolactone are added for the purpose of sterilization.

11. A method of visco-supplementation in a patient in need thereof, said method comprising intra-articular injection of a polymer solution according to claim 1 to the patient.

12. A method of using a polymer solution according to claim 1 as a support for pharmaceutical agents comprising adding one or more pharmaceutical agents to the polymer solution according to claim 1.

13. A polymer solution comprising:
   a) at least one hyaluronic acid or hyaluronic acid derivative having a molar mass $M_n$ ranging from 500,000 to 3,000,000 Dalton;
   b) at least one water-soluble alkali salt or alkaline earth salt of polystyrene sulfonic acid; and
   c) water;
   wherein the polymer solution comprises a) and b) in a mass ratio of a):b) of 1:1 to 1:0.001; and
   wherein the polymer solution is suitable for visco-supplementation.

14. The polymer solution according to claim 13, wherein the polymer solution is additionally clear to the eye, not discolored, and not degraded by hyaluronidase at 37° C. for at least 5 hours.

* * * * *